(12) United States Patent
Baker et al.

(10) Patent No.: US 12,390,253 B2
(45) Date of Patent: Aug. 19, 2025

(54) VARIABLE ANGLE LOCKING IMPLANT

(71) Applicant: Smith & Nephew, Inc., Memphis, TN (US)

(72) Inventors: Charles R. Baker, Lakeland, TN (US); Ryan Stevenson, Southaven, MS (US); Darin S. Gerlach, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 440 days.

(21) Appl. No.: 17/734,002

(22) Filed: Apr. 30, 2022

(65) Prior Publication Data

US 2022/0265329 A1    Aug. 25, 2022

Related U.S. Application Data

(63) Continuation of application No. 16/569,204, filed on Sep. 12, 2019, now abandoned, which is a continuation of application No. 15/970,747, filed on May 3, 2018, now Pat. No. 10,448,980, which is a continuation of application No. 13/524,506, filed on Jun. 15, 2012, now abandoned.

(60) Provisional application No. 61/497,180, filed on Jun. 15, 2011.

(51) Int. Cl.
    *A61B 17/80*    (2006.01)
(52) U.S. Cl.
    CPC .................. *A61B 17/8052* (2013.01)
(58) Field of Classification Search
    None
    See application file for complete search history.

(56) References Cited

U.S. PATENT DOCUMENTS

| | | | |
|---|---|---|---|
| 300,146 | A | 6/1884 | Sinnett |
| 351,751 | A | 11/1886 | Douglas |
| 382,670 | A | 5/1888 | Trovillion |
| 544,606 | A | 8/1895 | Balsley |

(Continued)

FOREIGN PATENT DOCUMENTS

| | | |
|---|---|---|
| CA | 2047521 A1 | 1/1992 |
| CA | 2408327 C | 3/2001 |

(Continued)

OTHER PUBLICATIONS

Decision of Rejection for Japanese Application No. 2014-516034, mailed Mar. 27, 2017.

(Continued)

*Primary Examiner* — Amy R Sipp
(74) *Attorney, Agent, or Firm* — KDW Firm PLLC

(57) ABSTRACT

A variable angle locking implant includes a bone plate having a lower surface, an upper surface, and at least one opening extending from the lower surface to the upper surface along an axis. The opening has a plurality of fins oriented along a plane. The axis is non-perpendicular to a tangent of a projection of the lower surface across the opening, the tangent defined at the intersection between the axis and the projected lower surface, and/or the plane is non-parallel to the tangent. The implant includes at least one fastener, and the plurality of fins are deflectable relative to a head portion of the fastener such that the fastener can be inserted and retained at any one of a plurality of angles.

18 Claims, 4 Drawing Sheets

(56) References Cited

U.S. PATENT DOCUMENTS

| | | |
|---|---|---|
| 545,331 A | 8/1895 | Balsley |
| 565,808 A | 8/1896 | Staples |
| 575,631 A | 1/1897 | Brooks |
| 583,158 A | 5/1897 | Upham |
| 637,990 A | 11/1899 | Hoepner |
| 651,949 A | 6/1900 | Lillie |
| 689,722 A | 12/1901 | Hoover |
| 766,270 A | 8/1904 | Lapham |
| 775,427 A | 11/1904 | Lusted, Sr. |
| 902,040 A | 10/1908 | Wyckoff |
| 1,025,008 A | 4/1912 | Miner |
| 1,105,105 A | 7/1914 | Sherman |
| 1,275,810 A | 8/1918 | White |
| 1,575,149 A | 3/1926 | Craig et al. |
| 1,755,588 A | 4/1930 | Bronk |
| 1,925,385 A | 9/1933 | Humes et al. |
| 2,010,913 A | 8/1935 | Bruce et al. |
| 2,133,859 A | 10/1938 | Hawley |
| 2,152,977 A | 4/1939 | John |
| 2,501,978 A | 3/1950 | Heins |
| 2,524,167 A | 10/1950 | Frank |
| 2,560,912 A | 7/1951 | George |
| 2,667,194 A | 1/1954 | Fischer et al. |
| 2,756,791 A | 7/1956 | Benjamin |
| 3,056,441 A | 10/1962 | Helms |
| 3,279,510 A | 10/1966 | Dreyer et al. |
| 3,347,293 A | 10/1967 | Clark |
| 3,409,058 A | 11/1968 | La |
| 3,547,114 A | 12/1970 | Haboush |
| 3,552,389 A | 1/1971 | Allgower et al. |
| 3,630,261 A | 12/1971 | Gley |
| 3,662,797 A | 5/1972 | Healis |
| 3,668,972 A | 6/1972 | Allgower et al. |
| 3,716,050 A | 2/1973 | Johnston |
| 3,739,825 A | 6/1973 | Knox |
| 3,741,205 A | 6/1973 | Markolf et al. |
| 3,744,488 A | 7/1973 | Cox |
| 3,779,240 A | 12/1973 | Kondo |
| 3,782,432 A | 1/1974 | Allen |
| 3,866,607 A | 2/1975 | Forsythe et al. |
| 3,906,550 A | 9/1975 | Rostoker et al. |
| 3,935,762 A | 2/1976 | Tudisco |
| RE28,841 E | 6/1976 | Allgower et al. |
| 4,059,102 A | 11/1977 | Devas |
| 4,060,114 A | 11/1977 | Matsushima |
| 4,096,896 A | 6/1978 | Engel |
| 4,219,015 A | 8/1980 | Steinemann |
| 4,246,811 A | 1/1981 | Bondhus et al. |
| 4,263,904 A | 4/1981 | Judet |
| 4,338,926 A | 7/1982 | Kummer et al. |
| 4,364,382 A | 12/1982 | Mennen |
| 4,388,921 A | 6/1983 | Sutter et al. |
| 4,408,601 A | 10/1983 | Wenk |
| RE31,628 E | 7/1984 | Allgower et al. |
| 4,484,570 A | 11/1984 | Sutter et al. |
| 4,493,317 A | 1/1985 | Klaue |
| 4,513,744 A | 4/1985 | Klaue |
| 4,535,658 A | 8/1985 | Molinari |
| 4,564,007 A | 1/1986 | Coombs et al. |
| 4,565,193 A | 1/1986 | Streli |
| 4,573,458 A | 3/1986 | Lower |
| 4,683,878 A | 8/1987 | Carter |
| 4,704,929 A | 11/1987 | Osada |
| 4,791,918 A | 12/1988 | Von |
| 4,797,948 A | 1/1989 | Milliorn et al. |
| 4,838,252 A | 6/1989 | Klaue |
| 4,927,421 A | 5/1990 | Goble et al. |
| 4,978,349 A | 12/1990 | Frigg |
| 4,988,350 A | 1/1991 | Herzberg |
| 5,002,544 A | 3/1991 | Klaue et al. |
| 5,006,120 A | 4/1991 | Carter |
| 5,041,114 A | 8/1991 | Chapman et al. |
| 5,053,036 A | 10/1991 | Perren et al. |
| 5,085,660 A | 2/1992 | Lin |
| 5,129,901 A | 7/1992 | Decoste |
| 5,151,103 A | 9/1992 | Tepic et al. |
| 5,190,544 A | 3/1993 | Chapman et al. |
| 5,192,281 A | 3/1993 | de la Caffiniere |
| 5,197,966 A | 3/1993 | Sommerkamp |
| 5,198,308 A | 3/1993 | Shelly et al. |
| 5,237,893 A | 8/1993 | Ryder et al. |
| 5,259,398 A | 11/1993 | Vrespa |
| 5,269,784 A | 12/1993 | Mast |
| 5,275,601 A | 1/1994 | Gogolewski et al. |
| 5,304,180 A | 4/1994 | Slocum |
| 5,312,410 A | 5/1994 | Miller et al. |
| 5,324,290 A | 6/1994 | Zdeblick et al. |
| 5,324,291 A | 6/1994 | Ries et al. |
| 5,356,410 A | 10/1994 | Pennig |
| 5,360,452 A | 11/1994 | Engelhardt et al. |
| 5,364,398 A | 11/1994 | Chapman et al. |
| 5,364,399 A | 11/1994 | Lowery et al. |
| 5,395,374 A | 3/1995 | Miller et al. |
| 5,415,658 A | 5/1995 | Kilpela et al. |
| 5,423,820 A | 6/1995 | Miller et al. |
| 5,423,826 A | 6/1995 | Coates et al. |
| 5,429,641 A | 7/1995 | Golfried |
| 5,431,659 A | 7/1995 | Ross et al. |
| 5,470,333 A | 11/1995 | Ray |
| 5,474,553 A | 12/1995 | Baumgart |
| 5,487,743 A | 1/1996 | Laurain et al. |
| 5,514,138 A | 5/1996 | McCarthy |
| 5,520,690 A | 5/1996 | Errico et al. |
| 5,522,902 A | 6/1996 | Yuan et al. |
| 5,527,310 A | 6/1996 | Cole et al. |
| 5,531,143 A | 7/1996 | Habermehl et al. |
| 5,531,746 A | 7/1996 | Errico et al. |
| 5,531,748 A | 7/1996 | de la Caffiniere |
| 5,534,932 A | 7/1996 | Van et al. |
| 5,536,127 A | 7/1996 | Pennig |
| 5,569,253 A | 10/1996 | Farris et al. |
| 5,578,034 A | 11/1996 | Estes |
| 5,591,168 A | 1/1997 | Jude et al. |
| 5,601,553 A | 2/1997 | Trebing et al. |
| 5,607,426 A | 3/1997 | Ralph et al. |
| 5,607,428 A | 3/1997 | Lin |
| 5,643,265 A | 7/1997 | Errico et al. |
| 5,647,873 A | 7/1997 | Errico et al. |
| 5,665,088 A | 9/1997 | Gil et al. |
| 5,665,089 A | 9/1997 | Dall et al. |
| 5,676,667 A | 10/1997 | Hausman |
| 5,702,399 A | 12/1997 | Kilpela et al. |
| 5,709,686 A | 1/1998 | Talos et al. |
| 5,713,900 A | 2/1998 | Benzel et al. |
| 5,725,588 A | 3/1998 | Errico et al. |
| 5,733,287 A | 3/1998 | Tepic et al. |
| 5,735,853 A | 4/1998 | Olerud |
| 5,741,258 A | 4/1998 | Klaue et al. |
| 5,749,872 A | 5/1998 | Kyle et al. |
| 5,769,850 A | 6/1998 | Chin |
| 5,772,662 A | 6/1998 | Chapman et al. |
| 5,776,196 A | 7/1998 | Matsuzaki et al. |
| 5,788,697 A | 8/1998 | Kilpela et al. |
| 5,797,912 A | 8/1998 | Runciman et al. |
| 5,810,823 A | 9/1998 | Klaue et al. |
| 5,824,247 A | 10/1998 | Tunc |
| 5,876,402 A | 3/1999 | Errico et al. |
| 5,888,204 A | 3/1999 | Ralph et al. |
| 5,893,856 A | 4/1999 | Jacob et al. |
| 5,902,305 A | 5/1999 | Beger et al. |
| 5,904,683 A | 5/1999 | Pohndorf et al. |
| 5,904,684 A | 5/1999 | Rooks |
| 5,925,047 A | 7/1999 | Errico et al. |
| 5,935,130 A | 8/1999 | Kilpela et al. |
| 5,935,133 A | 8/1999 | Wagner et al. |
| 5,938,664 A | 8/1999 | Winquist et al. |
| 5,954,722 A | 9/1999 | Bono |
| 5,960,681 A | 10/1999 | Anderson et al. |
| 5,961,524 A | 10/1999 | Crombie |
| 5,964,769 A | 10/1999 | Wagner et al. |
| 5,968,046 A | 10/1999 | Castleman |
| 5,968,047 A | 10/1999 | Reed |
| 5,976,141 A | 11/1999 | Haag et al. |
| 6,016,727 A | 1/2000 | Morgan |

(56) References Cited

U.S. PATENT DOCUMENTS

| | | |
|---|---|---|
| 6,019,762 A | 2/2000 | Cole |
| 6,022,352 A | 2/2000 | Vandewalle |
| 6,053,921 A | 4/2000 | Wagner et al. |
| 6,096,040 A | 8/2000 | Esser |
| 6,102,951 A | 8/2000 | Sutter et al. |
| 6,129,730 A | 10/2000 | Bono et al. |
| 6,176,861 B1 | 1/2001 | Bernstein et al. |
| 6,183,475 B1 | 2/2001 | Lester et al. |
| 6,193,721 B1 | 2/2001 | Michelson |
| 6,206,881 B1 | 3/2001 | Frigg et al. |
| 6,214,049 B1 | 4/2001 | Gayer et al. |
| 6,228,085 B1 | 5/2001 | Theken et al. |
| 6,235,033 B1 | 5/2001 | Brace et al. |
| RE37,249 E | 6/2001 | Leibinger et al. |
| 6,258,092 B1 | 7/2001 | Dall |
| 6,273,889 B1 | 8/2001 | Richelsoph |
| 6,302,001 B1 | 10/2001 | Karle |
| 6,302,883 B1 | 10/2001 | Bono |
| 6,306,136 B1 | 10/2001 | Baccelli |
| 6,306,140 B1 | 10/2001 | Siddiqui |
| 6,309,393 B1 | 10/2001 | Tepic et al. |
| 6,322,562 B1 | 11/2001 | Wolter |
| 6,342,055 B1 | 1/2002 | Eisermann et al. |
| 6,355,041 B1 | 3/2002 | Martin |
| 6,355,043 B1 | 3/2002 | Adam |
| 6,358,250 B1 | 3/2002 | Orbay |
| 6,361,537 B1 | 3/2002 | Anderson |
| 6,364,885 B1 | 4/2002 | Kilpela et al. |
| 6,370,091 B1 | 4/2002 | Kuroda |
| 6,379,359 B1 | 4/2002 | Dahners |
| 6,386,808 B2 | 5/2002 | Fujii et al. |
| 6,391,030 B1 | 5/2002 | Wagner et al. |
| 6,413,259 B1 | 7/2002 | Lyons et al. |
| 6,428,542 B1 | 8/2002 | Michelson |
| 6,436,100 B1 | 8/2002 | Berger |
| 6,440,135 B2 | 8/2002 | Orbay et al. |
| 6,454,769 B2 | 9/2002 | Wagner et al. |
| 6,454,770 B1 | 9/2002 | Klaue |
| 6,468,278 B1 | 10/2002 | Muckter |
| 6,475,218 B2 | 11/2002 | Gournay et al. |
| 6,506,191 B1 | 1/2003 | Joos |
| 6,520,965 B2 | 2/2003 | Chervitz et al. |
| 6,524,238 B2 | 2/2003 | Velikaris et al. |
| 6,527,776 B1 | 3/2003 | Michelson |
| 6,558,387 B2 | 5/2003 | Errico et al. |
| 6,575,975 B2 | 6/2003 | Brace et al. |
| 6,595,993 B2 | 7/2003 | Donno et al. |
| 6,595,994 B2 | 7/2003 | Kilpela et al. |
| 6,605,090 B1 | 8/2003 | Trieu et al. |
| 6,623,486 B1 | 9/2003 | Weaver et al. |
| 6,669,700 B1 | 12/2003 | Farris et al. |
| 6,669,701 B2 | 12/2003 | Steiner et al. |
| 6,682,531 B2 | 1/2004 | Winquist et al. |
| 6,682,533 B1 | 1/2004 | Dinsdale et al. |
| 6,684,741 B2 | 2/2004 | Blackston |
| 6,689,133 B2 | 2/2004 | Morrison et al. |
| 6,692,498 B1 | 2/2004 | Niiranen et al. |
| 6,692,581 B2 | 2/2004 | Tong et al. |
| 6,719,759 B2 | 4/2004 | Wagner et al. |
| 6,730,091 B1 | 5/2004 | Pfefferle et al. |
| 6,755,829 B1 | 6/2004 | Bono et al. |
| 6,767,351 B2 | 7/2004 | Orbay et al. |
| 6,780,186 B2 | 8/2004 | Errico et al. |
| 6,821,278 B2 | 11/2004 | Frigg et al. |
| 6,866,665 B2 | 3/2005 | Orbay |
| 6,893,443 B2 | 5/2005 | Frigg et al. |
| 6,893,444 B2 | 5/2005 | Orbay |
| 6,916,320 B2 | 7/2005 | Michelson |
| 6,945,975 B2 | 9/2005 | Dalton |
| 6,955,677 B2 | 10/2005 | Dahners |
| 6,960,213 B2 | 11/2005 | Chervitz et al. |
| 6,969,390 B2 | 11/2005 | Michelson |
| 6,973,860 B2 | 12/2005 | Nish |
| 6,974,461 B1 | 12/2005 | Wolter |
| 6,979,334 B2 | 12/2005 | Dalton |
| 7,073,415 B2 | 7/2006 | Casutt et al. |
| 7,074,221 B2 | 7/2006 | Michelson |
| 7,128,744 B2 | 10/2006 | Weaver et al. |
| 7,172,593 B2 | 2/2007 | Trieu et al. |
| 7,179,260 B2 | 2/2007 | Gerlach et al. |
| 7,230,039 B2 | 6/2007 | Trieu et al. |
| 7,250,053 B2 | 7/2007 | Orbay |
| 7,250,054 B2 | 7/2007 | Allen et al. |
| 7,255,701 B2 | 8/2007 | Allen et al. |
| 7,282,053 B2 | 10/2007 | Orbay |
| 7,294,130 B2 | 11/2007 | Orbay |
| 7,341,589 B2 | 3/2008 | Weaver et al. |
| 7,419,714 B1 | 9/2008 | Magerl et al. |
| 7,637,928 B2 | 12/2009 | Fernandez |
| 7,695,472 B2 | 4/2010 | Young |
| 7,722,653 B2 | 5/2010 | Young et al. |
| 7,766,948 B1 | 8/2010 | Leung |
| 8,105,367 B2 | 1/2012 | Austin et al. |
| 8,992,581 B2 | 3/2015 | Austin et al. |
| 2001/0037112 A1 | 11/2001 | Brace et al. |
| 2001/0047174 A1 | 11/2001 | Donno et al. |
| 2002/0013587 A1 | 1/2002 | Winquist et al. |
| 2002/0045901 A1 | 4/2002 | Wagner et al. |
| 2002/0058940 A1 | 5/2002 | Frigg et al. |
| 2002/0058943 A1 | 5/2002 | Kilpela et al. |
| 2002/0115742 A1 | 8/2002 | Trieu et al. |
| 2002/0143338 A1 | 10/2002 | Orbay et al. |
| 2002/0161370 A1 | 10/2002 | Frigg et al. |
| 2003/0040749 A1 | 2/2003 | Grabowski et al. |
| 2003/0057590 A1 | 3/2003 | Loher et al. |
| 2003/0060827 A1 | 3/2003 | Coughln |
| 2003/0105462 A1 | 6/2003 | Haider |
| 2003/0183335 A1 | 10/2003 | Winniczek et al. |
| 2004/0010257 A1 | 1/2004 | Cachia et al. |
| 2004/0030342 A1 | 2/2004 | Trieu et al. |
| 2004/0044345 A1 | 3/2004 | DeMoss et al. |
| 2004/0059334 A1 | 3/2004 | Weaver et al. |
| 2004/0059335 A1 | 3/2004 | Weaver et al. |
| 2004/0073218 A1 | 4/2004 | Dahners |
| 2004/0087954 A1 | 5/2004 | Allen et al. |
| 2004/0097942 A1 | 5/2004 | Allen et al. |
| 2004/0138666 A1 | 7/2004 | Molz et al. |
| 2004/0181228 A1 | 9/2004 | Wagner et al. |
| 2004/0186477 A1 | 9/2004 | Winquist et al. |
| 2004/0199169 A1 | 10/2004 | Koons et al. |
| 2004/0213645 A1 | 10/2004 | Kovac |
| 2004/0215195 A1 | 10/2004 | Shipp et al. |
| 2004/0220570 A1 | 11/2004 | Frigg |
| 2004/0236332 A1 | 11/2004 | Frigg |
| 2004/0254579 A1* | 12/2004 | Buhren ............... A61B 17/8033 606/71 |
| 2004/0260306 A1 | 12/2004 | Fallin et al. |
| 2005/0010220 A1 | 1/2005 | Casutt et al. |
| 2005/0010226 A1 | 1/2005 | Grady et al. |
| 2005/0027298 A1 | 2/2005 | Michelson |
| 2005/0043736 A1 | 2/2005 | Mathieu et al. |
| 2005/0049593 A1 | 3/2005 | Duong et al. |
| 2005/0049594 A1 | 3/2005 | Wack et al. |
| 2005/0070904 A1 | 3/2005 | Gerlach et al. |
| 2005/0080421 A1 | 4/2005 | Weaver et al. |
| 2005/0107796 A1 | 5/2005 | Gerlach et al. |
| 2005/0137597 A1 | 6/2005 | Butler et al. |
| 2005/0149026 A1 | 7/2005 | Buller et al. |
| 2005/0165400 A1 | 7/2005 | Fernandez |
| 2005/0192580 A1 | 9/2005 | Dalton |
| 2005/0222570 A1 | 10/2005 | Jackson |
| 2005/0234457 A1 | 10/2005 | James et al. |
| 2005/0261688 A1 | 11/2005 | Grady et al. |
| 2005/0277937 A1 | 12/2005 | Leung et al. |
| 2005/0283154 A1 | 12/2005 | Orbay et al. |
| 2006/0004361 A1 | 1/2006 | Hayeck et al. |
| 2006/0009770 A1 | 1/2006 | Speirs et al. |
| 2006/0009771 A1 | 1/2006 | Orbay et al. |
| 2006/0095040 A1 | 5/2006 | Schlienger et al. |
| 2006/0116678 A1 | 6/2006 | Impellizzeri |
| 2006/0122602 A1 | 6/2006 | Konieczynski et al. |
| 2006/0129148 A1 | 6/2006 | Simmons et al. |
| 2006/0129151 A1 | 6/2006 | Allen et al. |
| 2006/0149265 A1 | 7/2006 | James et al. |

(56) References Cited

U.S. PATENT DOCUMENTS

| | | | |
|---|---|---|---|
| 2006/0165400 A1 | 7/2006 | Spencer |
| 2006/0167464 A1 | 7/2006 | Allen et al. |
| 2006/0200147 A1 | 9/2006 | Ensign et al. |
| 2006/0235400 A1 | 10/2006 | Schneider |
| 2006/0235410 A1 | 10/2006 | Ralph et al. |
| 2006/0259039 A1 | 11/2006 | Pitkanen et al. |
| 2007/0010817 A1 | 1/2007 | de Coninck |
| 2007/0043366 A1 | 2/2007 | Pfefferle et al. |
| 2007/0093836 A1 | 4/2007 | Derouet |
| 2007/0142921 A1 | 6/2007 | Lewis et al. |
| 2007/0161995 A1 | 7/2007 | Trautwein et al. |
| 2007/0162016 A1 | 7/2007 | Matityahu |
| 2007/0162020 A1 | 7/2007 | Gerlach et al. |
| 2007/0185488 A1 | 8/2007 | Pohjonen et al. |
| 2007/0213828 A1 | 9/2007 | Trieu et al. |
| 2007/0233106 A1 | 10/2007 | Horan et al. |
| 2007/0260244 A1 | 11/2007 | Wolter |
| 2007/0270691 A1 | 11/2007 | Bailey et al. |
| 2007/0270832 A1 | 11/2007 | Moore |
| 2007/0270833 A1 | 11/2007 | Bonutti et al. |
| 2007/0276383 A1 | 11/2007 | Rayhack |
| 2008/0021474 A1 | 1/2008 | Bonutti et al. |
| 2008/0039845 A1 | 2/2008 | Bonutti et al. |
| 2008/0086129 A1 | 4/2008 | Lindemann et al. |
| 2008/0140130 A1 | 6/2008 | Chan et al. |
| 2008/0154367 A1 | 6/2008 | Justis et al. |
| 2008/0154368 A1 | 6/2008 | Justis et al. |
| 2008/0154373 A1 | 6/2008 | Protopsaltis et al. |
| 2008/0167717 A9 | 7/2008 | Trieu et al. |
| 2008/0200955 A1 | 8/2008 | Tepic |
| 2008/0208259 A1 | 8/2008 | Gilbert et al. |
| 2008/0234677 A1 | 9/2008 | Dahners et al. |
| 2008/0234748 A1 | 9/2008 | Wallenstein et al. |
| 2008/0234751 A1 | 9/2008 | McClintock |
| 2008/0300637 A1 | 12/2008 | Austin et al. |
| 2009/0024161 A1 | 1/2009 | Bonutti et al. |
| 2009/0076553 A1 | 3/2009 | Wolter |
| 2009/0088807 A1 | 4/2009 | Castaneda et al. |
| 2009/0143824 A1 | 6/2009 | Austin et al. |
| 2009/0149888 A1 | 6/2009 | Abdelgany |
| 2009/0192549 A1 | 7/2009 | Sanders et al. |
| 2009/0312803 A1* | 12/2009 | Austin | A61B 17/8014 606/86 R |
| 2010/0057138 A1* | 3/2010 | Murner | A61B 17/1728 606/108 |
| 2010/0256686 A1 | 10/2010 | Fisher et al. |
| 2010/0312286 A1 | 12/2010 | Dell'Oca |
| 2011/0015681 A1 | 1/2011 | Elsbury |
| 2012/0059425 A1 | 3/2012 | Biedermann |
| 2012/0083847 A1 | 4/2012 | Huebner et al. |
| 2012/0136396 A1 | 5/2012 | Baker et al. |
| 2012/0143193 A1 | 6/2012 | Hulliger |
| 2012/0265253 A1 | 10/2012 | Conley et al. |
| 2013/0165977 A1 | 6/2013 | Biedermann et al. |

FOREIGN PATENT DOCUMENTS

| | | |
|---|---|---|
| CA | 2536960 A1 | 3/2005 |
| CH | 611147 A5 | 5/1979 |
| CN | 1380043 A | 11/2002 |
| DE | 2602900 C3 | 4/1979 |
| DE | 3513600 A1 | 10/1986 |
| DE | 3804749 A1 | 3/1989 |
| DE | 3832343 A1 | 3/1990 |
| DE | 4341980 A1 | 6/1995 |
| DE | 4343117 A1 | 6/1995 |
| DE | 4438261 C1 | 9/1995 |
| DE | 4438264 C2 | 11/1996 |
| DE | 19629011 A1 | 1/1998 |
| DE | 102005015496 A1 | 11/2006 |
| DE | 102005042766 A1 | 1/2007 |
| DE | 19858889 B4 | 8/2008 |
| EP | 0201024 A1 | 11/1986 |
| EP | 0207884 A2 | 1/1987 |
| EP | 0274713 A1 | 7/1988 |
| EP | 0355035 A2 | 2/1990 |
| EP | 0468192 A3 | 4/1992 |
| EP | 0486762 B1 | 5/1995 |
| EP | 0530585 B1 | 12/1996 |
| EP | 0760632 A1 | 3/1997 |
| EP | 0799124 B1 | 8/2001 |
| EP | 1813292 A1 | 8/2007 |
| EP | 1857073 A1 | 11/2007 |
| FR | 2667913 A1 | 4/1992 |
| FR | 2698261 B1 | 3/1995 |
| FR | 2739151 B1 | 11/1997 |
| FR | 2757370 A1 | 6/1998 |
| FR | 2963396 A1 | 2/2012 |
| GB | 580571 A | 9/1946 |
| GB | 2521346 A | 6/2015 |
| JP | 2003509107 A | 3/2003 |
| RU | 2234878 C2 | 8/2004 |
| SU | 1279626 A1 | 12/1986 |
| TW | 477687 B | 3/2002 |
| WO | WO1989004150 A1 | 5/1989 |
| WO | WO1990007304 A1 | 7/1990 |
| WO | WO1996009014 A1 | 3/1996 |
| WO | WO1996019336 A1 | 6/1996 |
| WO | WO1996025892 A1 | 8/1996 |
| WO | WO1996029948 A1 | 10/1996 |
| WO | WO1997009000 A1 | 3/1997 |
| WO | WO1998034553 A1 | 8/1998 |
| WO | WO1998034556 A1 | 8/1998 |
| WO | WO1999005968 A1 | 2/1999 |
| WO | WO1999025266 A1 | 5/1999 |
| WO | WO1999061081 A1 | 12/1999 |
| WO | WO2000018309 A1 | 4/2000 |
| WO | WO2000019264 A1 | 4/2000 |
| WO | WO2000036984 A1 | 6/2000 |
| WO | WO2000053110 A1 | 9/2000 |
| WO | WO2000053111 A1 | 9/2000 |
| WO | WO2000066012 A1 | 11/2000 |
| WO | WO2001019267 A1 | 3/2001 |
| WO | WO2001019268 A1 | 3/2001 |
| WO | WO2001019264 A1 | 8/2001 |
| WO | WO2001078615 A1 | 10/2001 |
| WO | WO2001091660 A1 | 12/2001 |
| WO | WO2002000127 A1 | 1/2002 |
| WO | WO2002058574 A2 | 8/2002 |
| WO | WO2002068009 A2 | 9/2002 |
| WO | WO2002034159 A3 | 11/2002 |
| WO | WO2002096309 A1 | 12/2002 |
| WO | WO2003006210 A1 | 1/2003 |
| WO | WO2003106110 A1 | 12/2003 |
| WO | WO2004032726 A2 | 4/2004 |
| WO | WO2004032751 A3 | 5/2004 |
| WO | WO2004086990 A1 | 10/2004 |
| WO | WO2004089233 A1 | 10/2004 |
| WO | 2004/107957 A2 | 12/2004 |
| WO | WO2005018471 A1 | 3/2005 |
| WO | WO2005018472 A1 | 3/2005 |
| WO | WO2005032386 A1 | 4/2005 |
| WO | WO2005034722 A1 | 4/2005 |
| WO | WO2005079685 A1 | 9/2005 |
| WO | WO2005062902 A3 | 12/2005 |
| WO | WO2006007965 A1 | 1/2006 |
| WO | WO2006039636 A2 | 4/2006 |
| WO | WO2006068775 A2 | 6/2006 |
| WO | WO2007014279 A2 | 2/2007 |
| WO | WO2007025520 A1 | 3/2007 |
| WO | WO2007041686 A1 | 4/2007 |
| WO | WO2007014192 A3 | 5/2007 |
| WO | WO2007092869 A2 | 8/2007 |
| WO | WO2007130840 A1 | 11/2007 |
| WO | WO200802213 A1 | 1/2008 |
| WO | WO2008033742 A1 | 3/2008 |
| WO | WO2008077137 A1 | 6/2008 |
| WO | WO2008079846 A1 | 7/2008 |
| WO | WO2008079864 A1 | 7/2008 |
| WO | WO2008116203 A3 | 12/2008 |

(56) References Cited

FOREIGN PATENT DOCUMENTS

| | | |
|---|---|---|
| WO | WO2009029908 A1 | 3/2009 |
| WO | WO2013/059090 A1 | 4/2013 |

OTHER PUBLICATIONS

Office Action for U.S. Appl. No. 14/605,651, mailed Oct. 6, 2016.
Office Action for U.S. Appl. No. 14/535,573, mailed Oct. 24, 2016.
Patent Examination Report No. 2 for Australian Application No. 2012271441, issued Sep. 28, 2016.
Office Action for Russian Application No. 2013158111/14(090494), mailed May 17, 2016, with English-language synopsis.
Office Action for U.S. Appl. No. 14/671,499, mailed Jun. 2, 2016.
Office Action for U.S. Appl. No. 14/535,573, mailed Mar. 31, 2016.
Office Action for U.S. Appl. No. 14/605,651, mailed Mar. 14, 2016.
Notice of Reasons for Rejection for Japanese Application No. 2014-516034 mailed Jun. 6, 2016.
Office Action for Chinese Application No. 201280039748.1, mailed Mar. 17, 2016.
Office Action for U.S. Appl. No. 14/535,573, mailed Oct. 1, 2015.
Notice of Reasons for Rejection for Japanese Application No. 2013-037623, mailed Jan. 26, 2015.
Notice of Reasons for Rejection for Japanese Application No. 2013-037623, mailed Mar. 3, 2014.
Wolter, D., et al., "Universal Internal Titanium Fixation Device," Trauma Berufskrankh (1999) 1:307-309, Springer-Verlag 1999, Certified English Translation Thereof.
Bohmer, G., et al., "Ti Fix® Angularly Stable Condylar Plate," Trauma Berufskrankh (1999) 1 :351-355, Springer-Verlag 1999, Certified English Translation Thereof.
Kranz, H.-W., et al., "Internal Titanium Fixation of Tibial Pseudarthrosis, Malalignment, and Fractures," Trauma Berufskrankh (1999) 1 :356-360, Springer-Verlag 1999, Certified English Translation Thereof.
Fuchs, S., et al., "Clinical Experiences with a New Internal Titanium Fixator for Ventral Spondylodesis of the Cervical Spine," Trauma Berufskrankh (1999) 1 :382-386, Springer-Verlag 1999, Certified English Translation Thereof.
Jurgens, C., et al., "Special Indications for the Application of the Fixed Angle Internal Fixation in Femur Fractures," Trauma Berufskrankh (1999) 1 :387,391, Springer-Verlag 1999, Certified English Translation Thereof.
Wolter, D., et al., "Titanium Internal Fixator for the Tibia," Trauma Berufskrankh, Mar. 2001 (Supp 2): S156-S161, Springer-Verlag 2001, Certified English Translation Thereof.
Fuchs, S., et al., "Titanium Fixative Plate System with Multidirectional Angular Stability in the Lower Leg and Foot," Trauma Berufskrankh, Mar. 2001 (Suppl 4): S447-S453, Springer-Verlag 2001, Certified English Translation Thereof.
Office Action for U.S. Appl. No. 13/774,721, mailed Aug. 22, 2013.
Australian Office Action in Application No. 2013202741, issued Feb. 3, 2014, 4 pages.
Examiner's First Report on Australian Application No. 2006272646, mailed Mar. 21, 2011, 4 pages.
Smith & Nephew Brochure entitled 'Surgical Technique PERI-LOC VLP Variable-Angle Locked Plating System,' pp. 1-32 (Nov. 2007).
Smith & Nephew Brochure entitled 'PERI-LOC VLP Variable-Angle Locked Plating System Distal Tibia Locking Plates,' 04 pages (Oct. 2007).
Smith & Nephew Brochure entitled 'PERI-LOC VLP Variable-Angle Locked Plating System Distal Fibula Locking Plates,' 04 pages (Oct. 2007).

Smith & Nephew Brochure entitled 'PERI-LOC VLP Variable-Angle Locked Plating System Proximal Tibia Locking Plates,' 04 pages (Oct. 2007).
Smith & Nephew Brochure entitled 'PERI•LOC VLP Variable-Angle Locked Plating System Proximal Tibia Variable-Angle Locking Plates,' 04 pages (Nov. 2007).
Smith & Nephew Brochure entitled 'PERI-LOC VLP Variable-Angle Locked Plating System Improved Torsional Fatigue Properties with Thin Locked Versus Non-Locked Plate Constructs for Fixation of Simulated Osteoporotic Distal Fibula Fractures,' 04 pages (Nov. 2007).
Winkelstabilitat, litos Unidirectional locking screw technology, Jan. 15, 2008, 5 pages http://www.litos.com/pages/winkelsta bilitaet e.html.
"SMARTLock Locking Screw Technology," http://www.stryker.com/microimplants/products/cmf smartlock.phn, Mar. 14, 2004.
International Search Report for PCT /US2006/028778, dated Apr. 19, 2007.
"Fracture and Dislocation Compendium," Orthopaedic Trauma Association Committee for Coding and Classification, Journal of Orthopaedic Trauma, vol. 10, Suppl.,jp, v=ix, 1996.
English Abstract of JP 2002532185, Published Oct. 2, 2002.
English Abstract of ZA 200200992, Published Dec. 18, 2002, Applicant: Synthes AG.
NCB® Proximal Humerus Plating System, Surgical Technique, Zimmer, Inc. 2005.
Zimmer® NCB® Plating System, Zimmer, Inc. 2006.
NCB® Distal Femoral Plating System, Surgical Technique, Zimmer, Inc. 2005.
Office Action for Japanese Application No. 2008-0524048 mailed Oct. 25, 2011, 6 pages.
Office Action for U.S. Appl. No. 12/069,331 mailed Aug. 23, 2011, 12 pages.
International Preliminary Report on Patentability for International Application No. PCT/US2006/028778, mailed Jan. 29, 2008, 9 pages.
Office Action for U.S. Appl. No. 12/484,527, mailed May 18, 2011, 10 pages.
Office Action for U.S. Appl. No. 12/484,527, mailed Jan. 20, 2011, 9 pages.
DePuy brochure entitled "Every Surgeon has His or Her Own View," Stryker Numelock II® Polyaxial Locking System, Operative Technique, Gtrauma Application, 6 pages (undated).
"Polyax Wide Angle Freedom Surgical Technique Distal Femoral Locked Playing System," DePuy International Ltd., http://www /rcsed .ac.u k/fellows/Iva nrensbu rg/ classification/su rgtech/depuy (2005).
DePuy Orthopaedics, Inc., "Surgical Technique Distal Femoral Locked Plating System," Polyax Wide Angle Freedom (2005).
Machine Translation of EP 1649819.
Final Office Action for U.S. Appl. No. 12/069,331, mailed Apr. 9, 2012.
Office Action for U.S. Appl. No. 11/996,795, mailed Mar. 23, 2012.
Decision of Rejection for Japanese Application No. 2008-0524048, mailed Oct. 30, 2011.
Office Action for U.S. Appl. No. 11/996,795, mailed Nov. 21, 2012.
Office Action for Canadian Patent Application No. 2,839,423, mailed Dec. 6, 2018.
Final Office Action for Japanese Application No. 2017-145326, mailed Jan. 28, 2019.
Office Action for Japanese Patent Application No. 2017-145326, mailed Nov. 5, 2019.
Examination Report for Indian Patent Application No. 10688/DELNP/2013, mailed Jan. 17, 2020.

* cited by examiner

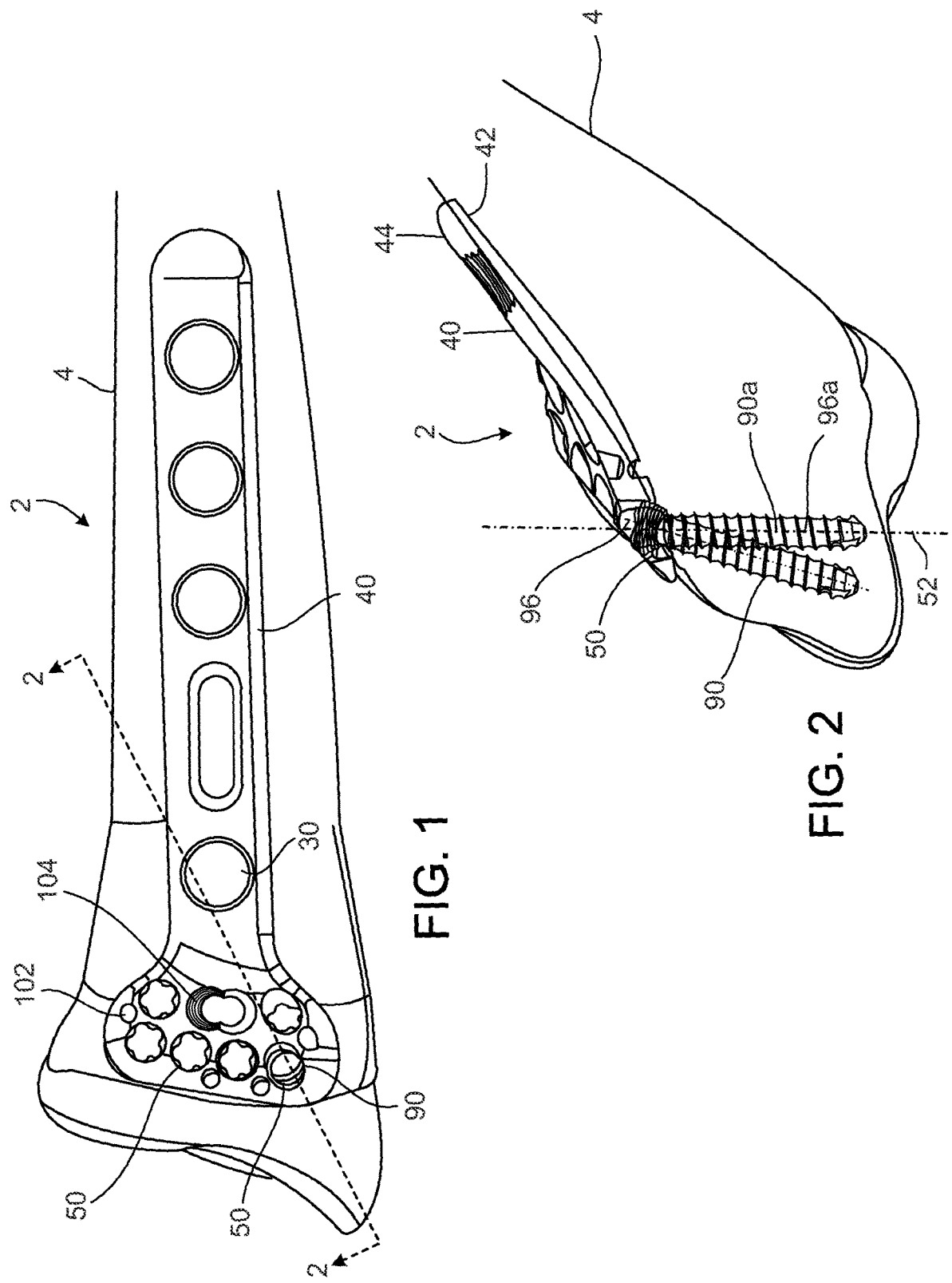

VARIABLE ANGLE LOCKING IMPLANT

CROSS-REFERENCE TO RELATED APPLICATIONS

This application is a continuation application of U.S. patent application Ser. No. 16/569,204, filed Sep. 12, 2019, entitled "Variable Angle Locking Implant", which is a continuation application of U.S. patent application Ser. No. 15/970,747, filed May 3, 2018, now U.S. Pat. No. 10,448,980, entitled "Variable Angle Locking Implant", which is a continuation application of U.S. patent application Ser. No. 13/524,506, filed Jun. 15, 2012, entitled "Variable Angle Locking Implant", which application claims priority to and the full benefit of U.S. Provisional Application Ser. No. 61/497,180 filed Jun. 15, 2011, and entitled "Variable Angle Locking Implant," the entire contents of each application incorporated herein by reference.

TECHNICAL FIELD

This invention relates to a variable angle locking implant.

BACKGROUND

Variable angle locking implants for repairing bone fractures have been described, for example, in U.S. patent application Ser. No. 12/484,527, filed Jun. 15, 2009, published as U.S. Publication No. 2009/0312803, hereby incorporated herein by reference in its entirety. In particular, U.S. Publication No. 2009/0312803 describes an implant having fastener receiving holes with fins that permit a fastener to be positioned off-axis within the hole.

Implants such as bone plates have been provided with threaded holes (that may receive either locking screws or non-locking screws), non-threaded holes (for non-locking screws), partially threaded slots to allow either non-locking or locking screws to be used together, and combinations of the above.

SUMMARY

The variable angle locking implant provides a stable connection between a bone and a bone plate using a fastener that permits different angles to be obtained between the bone plate and the fastener, while the fastener also locks into the bone plate. This allows the surgeon to reach denser areas of bone or capture random bone fragments that are in irregular positions, for example, in cases of severe fractures with highly fragmented bones. The fastener and plate system advantageously allows the surgeon to choose the angle at which the screw is inserted through, and rigidly affixed in, an opening of the plate.

The variable angle locking implant allows a surgeon to direct the fastener toward bone fragments that are not necessarily located along the axis of the opening in the plate. It also provides flexibility in the placement of the plate in relation to the bone fracture. Allowing surgeons to choose the angle at which the fastener is inserted into the plate leads to better tailoring of the system to the specific nature of the bone fracture to be treated, and allows surgeons to adjust their strategy as necessary after the surgical site has been accessed, but prior to insertion of the fastener into bone material.

According to one aspect, a variable angle locking implant includes a bone plate having a lower surface, an upper surface, and at least one opening extending from the lower surface to the upper surface along an axis. The opening has an inner surface with a plurality of fins oriented along a plane. The axis is non-perpendicular to a tangent of a projection of the lower surface across the opening, the tangent defined at the intersection between the axis and the projected lower surface, and/or the plane is non-parallel to the tangent.

Implementations of this aspect may include one or more of the following features.

For example, the lower surface includes a bone conforming arcuate surface. The lower surface is adapted to contact a distal femur, a proximal femur, a distal tibia, a proximal tibia, a proximal humerus, a distal humerus, a clavicle, a fibula, an ulna, a radius, a distal radius, a rib, pelvis, a vertebra, bones of the foot, or bones of the hand, shaft fractures on long bones, or any of the aforementioned adjacent bones in the case of a joint fusion plate.

The fins are positioned within the opening. The axis is perpendicular to the tangent and the plane is non-parallel to the tangent. Alternatively, the axis is non-perpendicular to the tangent and the plane is non-parallel to the tangent, for example, the plane is perpendicular to the axis.

The fins are integrally connected to, and protruding from, the inner surface. The opening has a radius between the inner surface and the top of the fins, and each fin tapers in thickness from the inner surface towards its terminal end. The opening has a jagged circumference formed by protruding fins at the lower surface. The protruding fins form a concave portion of the inner surface. The protruding fins have bases that meet the inner surface along the plane. The fins have a tapered shape or a straight shape. The fins are provided in more than one layer. The fins are trapezoidally-shaped, rounded, oval, rectangular, curved, rhomboid, diamond-shaped, or triangular. The edges of the fins taper inwardly, outwardly, or are about parallel with one another. There are at least 3, but no more than 10, fins integrally connected to, and protruding from, the inner surface. The fins are provided as a series of concavely indented, inwardly protruding fins that are adapted to secure a threaded head of a fastener in place at varying angles.

The bone plate includes one or more of the following openings: a threaded opening; a non-threaded opening; an opening adapted to receive locking or non-locking fasteners; an opening with fins; a provisional fixation opening; a combination slot; or any combination thereof.

The implant includes at least one fastener. The fastener is at least partially threaded and has a head portion and a shaft portion. The opening is adapted to receive the fastener without being tapped by the fastener. The plurality of fins are deflectable relative to the head portion of the fastener when the fastener is inserted into the opening such that the fastener can be inserted and retained at any one of a plurality of angles relative to the opening. The fins are deflectable so that the fins are interposed between the threads of the fastener. The inner surface includes threads located above or below the fins.

According to another aspect, a method for securing a bone plate to a bone includes placing a lower surface of the bone plate against the bone; inserting a fastener into an opening in the bone plate, the opening having an axis that is non-perpendicular to a tangent of a projection of the lower surface across the opening, the tangent defined at the intersection between the axis and the projected lower surface, selecting a trajectory of the fastener into the bone, the trajectory being up to about 15 degrees off the hole axis; and inserting the fastener into the bone.

Implementations of this aspect may include one or more of the following features.

For example, either a locking screw or a non-locking screw is inserted in the opening. The fastener is removed and re-inserted into the opening of the bone plate at any one of a plurality of angles. Inserting the fastener into the bone includes drawing a bone fragment into alignment with an intact bone segment.

The details of one or more implementations of the invention are set forth in the accompanying drawings and the description below. Other features, objects, and advantages of the invention will be apparent from the description and drawings, and from the claims.

BRIEF DESCRIPTION OF THE DRAWINGS

FIG. 1 is an illustration of a variable angle locking implant positioned on a bone.

FIG. 2 is a cross-sectional view of the variable angle locking implant taken along line 2-2 of FIG. 1.

DETAILED DESCRIPTION

Figure 3:
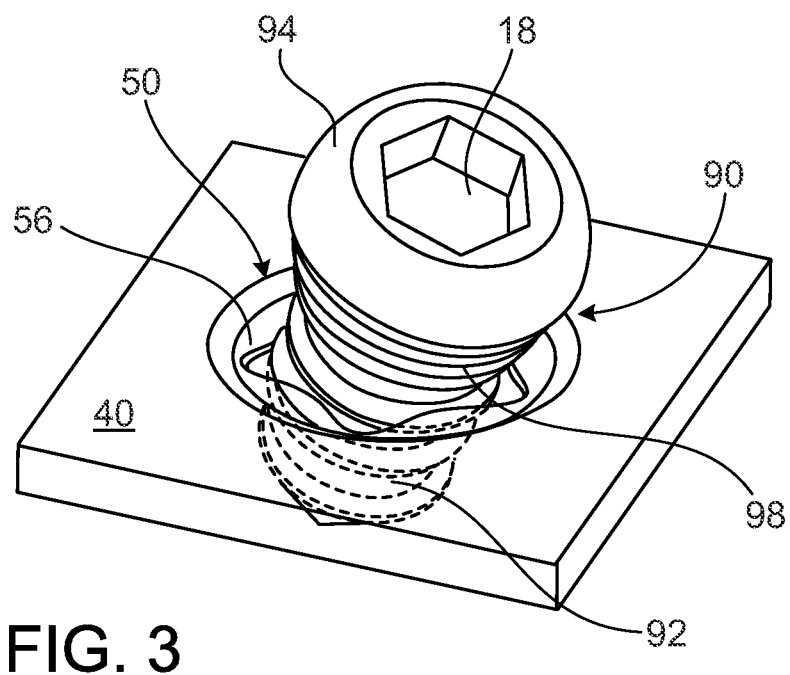
FIG. 3 is a perspective view of a bone plate and fastener of the variable angle locking implant.

Referring to FIGS. 1 and 2, a variable angle locking implant 2 for repairing fractures in bone 4 includes a bone plate 40 and one or more fasteners 90. A fastener 90 is shown engaged in a finned opening 50 that extends between an upper surface 44 and a lower, bone contacting surface 42 of the bone plate 40. The fastener 90 can be positioned in the opening 50 and fixed in the plate 40 at various insertion angles to capture "renegade" or random bone fragments that have split from the bone during fracture and secure the bone fragments to the plate 40.

The fastener 90 shows a new trajectory achieved by increasing the range of angles as compared to the screw 90a. For example, the central axis 96 of fastener 90 has an approximate 15 degree offset from the central axis 52 and approximately 30 degree offset from perpendicular to the lower surface 42 of the bone plate 40. The alternative placement of a screw 90a in a hole having an axis 52 perpendicular to the lower surface 42 of the plate 40 and a plane 59 that is parallel to the bottom lower surface 42 illustrates approximately a 15 degree offset from the central axis 52 and a corresponding approximately 15 degree offset from perpendicular to the lower surface 42 of the bone plate 40, thus illustrating the greater range of the insertion angle of the fastener 90.

The locking implant 2 also includes a provisional pin opening 102 as well as a combination slot 104.

Figure 4:
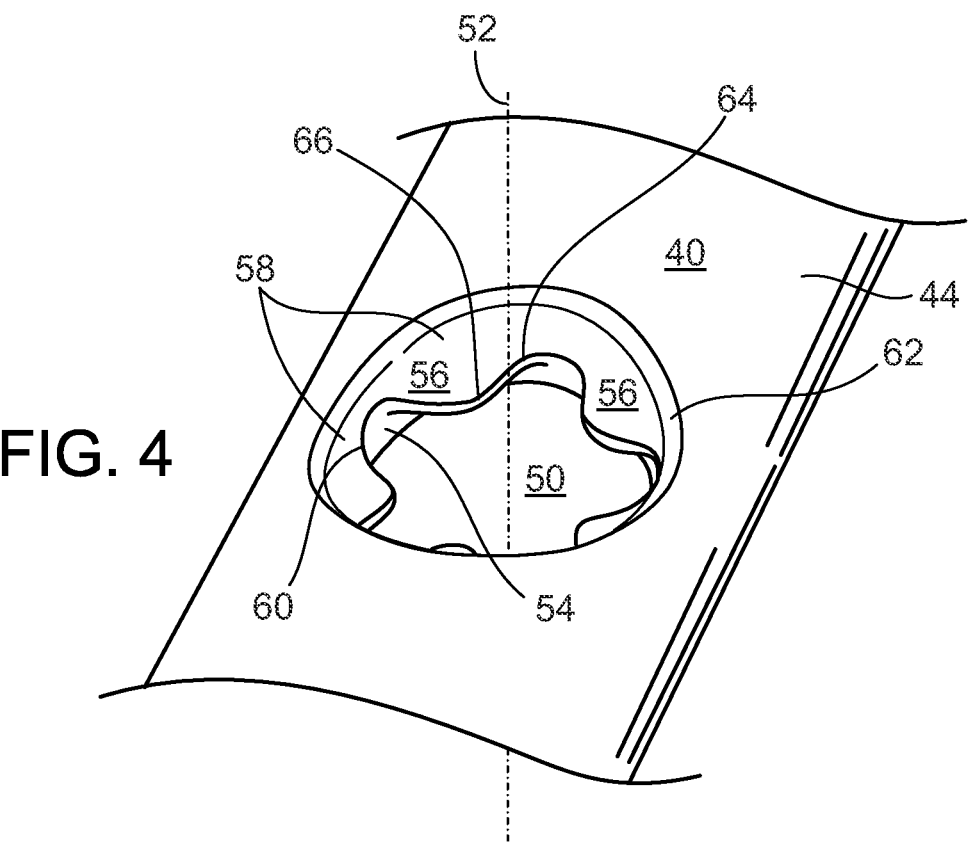
FIG. 4 is a perspective view of a bone plate of the variable angle locking implant having a finned opening.

Referring also to FIGS. 3 and 4, the plate 40 has an inner surface 54 that defines the opening 50 and a series of concavely indented, inwardly protruding fins 56 that extend toward a central axis 52 of the opening 50. Each fin 56 has a base 58 and the bases 58 form concave portions 60. The bases 58 of the fins 56 all meet, for example, in substantially the same plane 59a-59d (FIGS. 5A-5D) and then angle downwardly and inwardly at a similar angle or slope. As discussed further below, the central axis 52 can be oriented non-perpendicular to the lower surface 42 and/or the planes 59a-59d can be oriented non-parallel to the lower surface 42 to increase the range of possible insertion angles.

The concave portions 60 are smooth and non-threaded, and as illustrated, the entire inner surface 54 of the finned opening 50 can be devoid of threads. The lack of threads helps ease the manufacturing of the plate 40, and allows the plate 40 to be manufactured as thinly as desired. The bases 58 can extend from the inner surface 54 at or near an upper circumference 62 of the inner surface, at a middle region of the inner surface, or at or near a lower circumference of the inner surface. With the fins 56 located adjacent a lower circumference at the lower, bone contacting surface 42 of plate 40, the lower circumference appears jagged due to the presence of the fins, while the upper circumference 62 is smooth.

As the fins 56 extend toward central axis 52, they taper to form tapered sides 64. The fins 56 end at rounded tips 66, although tips 66 can be pointed, square, rectangular, or any other appropriate configuration. For example, as described in U.S. Patent Application Publication No. 2009/0312803, which is incorporated herein by reference in its entirety, the fins 56 can have straight edges or sides and straight ends such that the fins are partially rectangular-shaped with slit-shaped openings between the fins. Alternatively, the fins can be more triangular in shape having sides that taper inwardly and end edges that are flat and small. Other example fin shapes include trapezoidal, square, round, circular, triangular (with a pointed tip).

The dimensions of fins 56 are typically dependent at least in part upon the pitch and threads of the fastener 90. For example, a larger plate 40 for use with a larger fastener 90 (for example, for use on a femur bone) will likely be thicker and will have larger and thicker fins 56 than a smaller plate 40 (for example, for use on a smaller bone). In specific implementations, the fins 56 are particularly thin so that they can be moved up or down and deformed under pressure. In some implementations, the fins 56 may be pressed toward the edges of the finned opening 50. A non-limiting exemplary range of thicknesses for the fins 56 is from about 0.15 mm to about 5 mm, although larger and smaller sizes are possible. The fins 56 are intended to fit between threads 98 on the thread form of fastener 90, as shown in FIG. 3.

Providing a non-threaded inner surface 54 also allows the fastener 90 to be inserted into the finned opening 50 at any desired insertion angle, that is the angle defined between a longitudinal axis 96 (FIG. 2) of the fastener 90 and the central axis 52 (FIG. 4) of the finned opening 50. The central axis 52 and the longitudinal axis 96 can be co-linear so that the insertion angle is zero, or the central axis 52 and the longitudinal axis 96 (FIG. 1) can be non-co-linear with an insertion angle of up to about +/−15 degrees. Varying the insertion angle is possible because there are not any threads in the finned opening 50 to interfere with the desired insertion angle. The fins 56 are intended to slightly bend or deform in order to secure the fastener 90 in place in the finned opening 50. The fins 56 engage the threads 98 or other surface of the fastener 90.

The fastener 90 has a head 94 and a shaft 92. The shaft 92 may be threaded or non-threaded. The head 94 of the fastener 90 has at least one set of threads 98 and a bore 18 for receiving a driver in order to drive the fastener 90 through the plate 40 and into bone. The threads 98 are typically any standard-type thread.

Figure 5A:
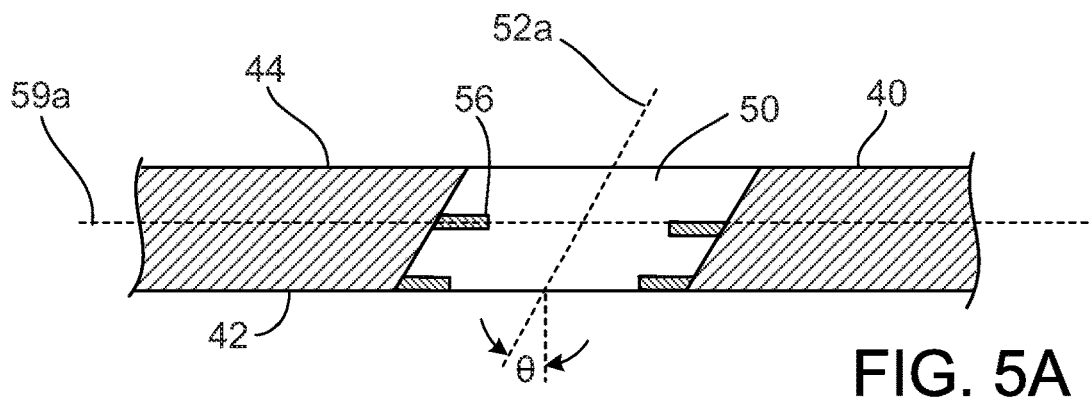
FIGS. 5A-5E are cross-sectional views of various implementations of the finned opening.
Figure 5B:
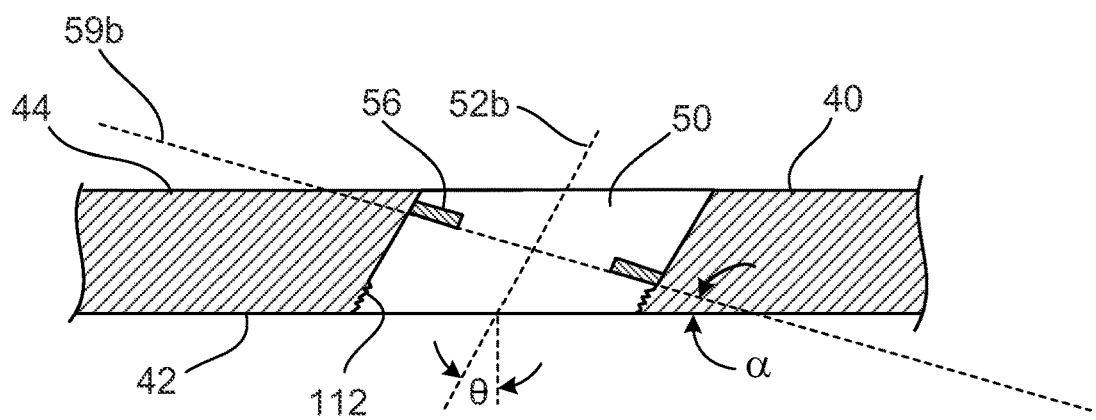
Figure 5C:
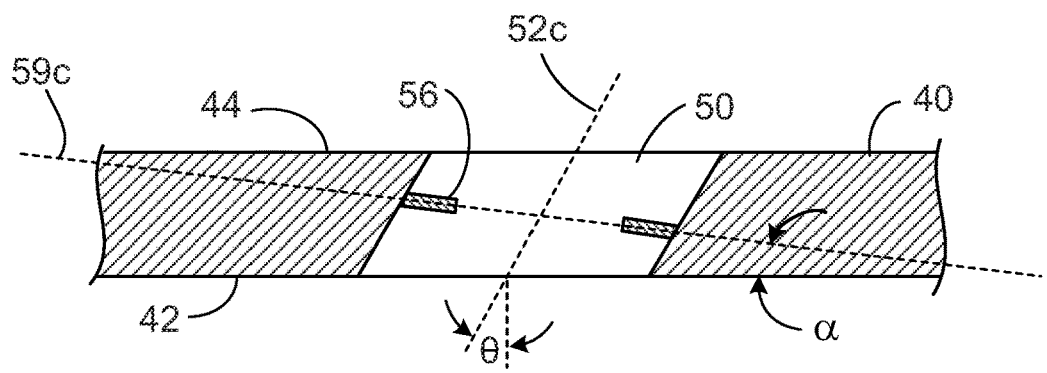

Referring to FIGS. 5A and 5B, the central axis 52a, 52b of the opening 50 can be oriented non-perpendicular to the lower surface 42 of the plate 40, for example, at an angle, Θ, in the range between 0 and 90 degrees. In FIG. 5A, two rows of fins 56 are illustrated that each lie in a plane 59a that is parallel to the lower surface 42 of the plate 40. In FIG. 5B, the fins 56 lie in a plane 59b that is oriented non-parallel to the lower surface 42 of the plate 40, for example, the plane 59b is perpendicular or nearly perpendicular to the axis 52b. In FIG. 5C, the fins 56 are illustrated lying in a plane 59c that is oriented non-parallel to the lower surface 42 of the plate 40 and the plane 59c is non-perpendicular to the axis 52c. The fins 56 of FIGS. 5B and 5C are positioned within the opening 50, that is, between the upper surface 44 and lower surface 42 of the plate 40.

The non-perpendicular orientation of the central axis 52a, 52b, 52d and/or the non-parallel orientation of the plane 59b-d increases the useful range of possible insertion angles as compared to a bone plate 40 having the central axis 52 perpendicular to the lower surface 42 and the plane 59 parallel to the lower surface 42. For example, referring to FIG. 5B, assuming Θ is 15 degrees, a fastener 90 could be inserted with the fastener axis 96 aligned with axis 52b, and thus 15 degrees off from perpendicular to the lower surface 42, or the fastener axis 96 could be tilted up to, for example, +/−15 degrees, such that the fastener axis 96 is perpendicular to the lower surface 42 or up to 30 degrees off from perpendicular to reach bone fragments. Increasing the range of angles allows the surgeon to target new fastener trajectories in the bone as shown in FIG. 2.

The screw 90 (FIG. 2) shows a new trajectory achieved by increasing the range of angles as compared to the screw 90a. The fastener 90 is shown positioned in the hole of FIG. 5B and having a 15 degree offset from the central axis 52 and 30 degree offset from perpendicular to the lower surface 42 of the bone plate 40. The alternative placement of a screw 90a in a hole having an axis 52 perpendicular to the lower surface 42 of the plate 40 and a plane 59 that is parallel to the lower surface 42 illustrates a 15 degree offset from the central axis 52 and only a corresponding 15 degree offset from perpendicular to the lower surface 42 of the bone plate 40, thus illustrating the greater range of the insertion angle of the fastener 90. Angling the screw greater than 15 degrees from the central axis 52 of an opening having an axis 52 perpendicular to the lower surface 42 of the plate 40 and a plane 59 that is parallel to the lower surface 42 produces inconsistent failure loads. Therefore, to achieve a screw trajectory greater than 15 degrees from the lower surface 42 of the plate 40 while maintaining the ability to capture and secure bone fragments, the angle of the central axis 52 is offset from perpendicular to the lower surface 42 and the screw axis 96 tilted to reach a maximum of 30 degrees offset.

Figure 5D:
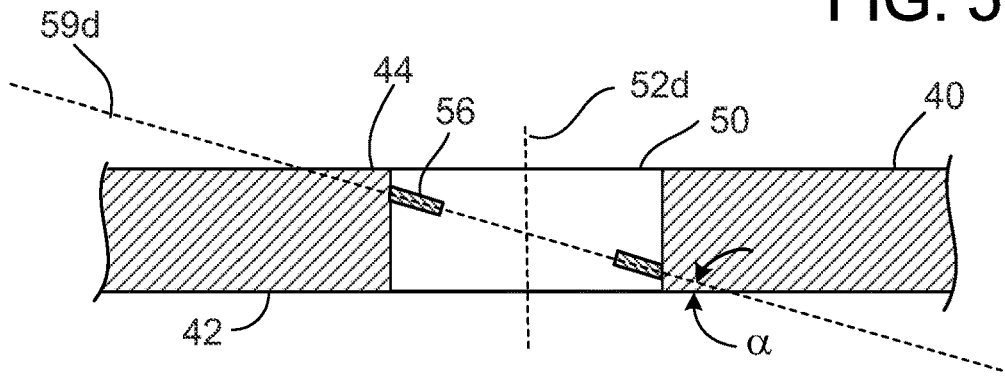

Referring to FIG. 5D, the range of insertion angles can also be increased by orienting the axis 52d of the opening 50 perpendicular to the lower surface 42 of the plate 40, while the fins 56 lie in a plane 59d that is non-parallel to the lower surface, for example, at an angle, α, in the range between 0 and 90 degrees.

The finned opening 50 can include about five to eight fins 56, as illustrated, two or three fins 56, or ten or twenty or more fins 56, depending upon the plate 40 for which the finned opening 50 is intended for use. The finned holes can optionally include threads 112 (FIG. 5B) formed above or below the fins in the inner surface of the hole. The region of the opening above the fins can taper inwardly from the upper surface of the plate, for example, at an angle of about 5 to 15 degrees, and the region of the opening below the fins can taper outwardly toward the lower surface of the plate, for example, at an angle of about 40 to 50 degrees. The finned opening 50 can optionally be a slot hole or combination hole with half or more of the length of the opening can be finned with the remainder of the opening being non-threaded for sliding compression.

The primary purpose of fins 56 is to grasp one or more threads 98 of the fastener 90 in order to secure the fastener 90 in place in the bone plate 40 at any desired insertion angle. Fasteners 90 received in different finned openings 50 can be inserted at the same or different insertion angles. As a fastener 90 is inserted, its threads 98 start to engage the fins 56, as shown in FIG. 3. As discussed above, the fins 56 can be very thin so that as the threads 98 start to grab the fins 56, the fins 56 can move up or down as appropriate to engage the threads 98 and secure the fastener 90 in the finned opening 50. The threads 98 engage the fins 56 so that the fins 56 fit between the threads 98. The movement of fins 56 can be a permanent deformation, so that the fins 56 cannot flex back and allow the fastener 90 to work its way out.

The finned openings 50 can be provided on all types of bone plates 40 and can be combined with other types of openings. As illustrated in FIG. 1, there can be finned openings 50, a threaded opening 30, and a provisional pin opening 102. Other options are holes that can be used with either a threaded or non-threaded fastener, as well as combination slots 104. For example, a slot having fins mounted on either or both ends of the slot for static locking and no threads or fins in the middle portion of the slot for dynamic locking These various types of openings may be used on any type of bone plate, in any combination and in any size. The inclusion of a plurality of finned openings 50 in the bone plate 40 can help achieve better fixation of a fractured bone, for example, where numerous fragments have shattered in various directions, because the fasteners 90 can be inserted at various angles to capture "renegade" or random bone fragments that have split from the bone during fracture, but still secure the bone fragments to the plate 40.

The threads 98 on fastener 90 can be any type of standard or non-standard thread. For example, the threads 98 can be a continuous ridge or a non-continuous ridge. The threads 98 can form a portion of a revolution, one complete revolution, multiple revolutions, a single lead, or multiple leads, or any other threads known in the art. Additionally or alternatively, the head 94 of fastener 90 can include any other surface that will engage with and seat within the fins 56 of the finned opening 50. For example, the head 94 can have a series of dimples, ridges, bumps, textured areas, or any other surface that can secure fastener 90.

The fastener 90 may be any typical fastener, made out of any appropriate material. The fastener 90 typically has a bore 18 for receiving a driver in order to drive the fastener 90 through the plate 40 and into bone. The bore 18 may be any size and shape, for example, it may have a hexagonal configuration to receive a corresponding hexagonal driver, a Phillips screw head, a flat-head, a star configuration, Torx, or any other appropriate configuration that can cooperate with a driver to drive the fastener 90 into the plate 40.

The shaft 92 may be fully threaded, partially threaded, or a helical blade, and/or may include one or more tacks, deployable talons, expandable elements, or any feature that allows shaft 92 to engage bone. It is also possible that shaft 92 is not threaded, so that fastener 90 takes the form of a peg or a pin. This alternative implementation may be preferred in certain procedures where, for instance, the main goal is to prevent tilting of a bone segment or in procedures where there is no concern of fastener 90 pulling out from the bone and hence no need for shaft 92 to be threaded or otherwise configured to engage bone. The end of shaft 92 may be a self-tapping or self-drilling tip.

Figure 5E:
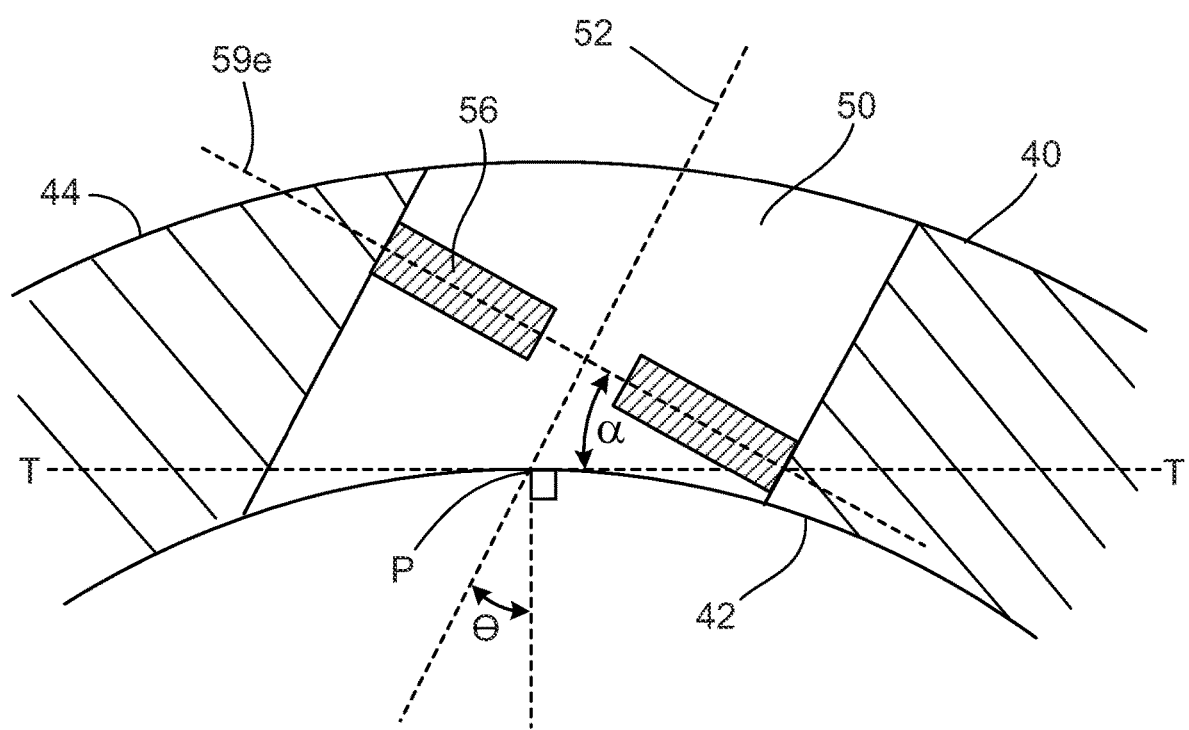

The bone plate 40 may be adapted to contact one or more of a distal femur, a proximal femur, a distal tibia, a proximal tibia, a proximal humerus, a distal humerus, a clavicle, a fibula, an ulna, a radius, a distal radius, a rib, pelvis, a vertebra, bones of the foot, or bones of the hand, shaft fractures on long bones, or any of the aforementioned adjacent bones in the case of a joint fusion plate. The bone plate 40 may be curved, contoured, straight, or flat. The lower, bone contacting surface 42 can have an arcuate shape that conforms to the bone. For example, referring to FIG. 5E, the bone plate 40 is shown with a bone contacting surface 42 having an arcuate or curved shape. In the implementation shown, the central axis 52 of the opening 50 can be oriented non-perpendicular to a tangent line or tangent plane T-T of the projected arcuate bone contacting surface 42 that intersects the central axis 52 at a point P along the projected bone contacting surface 42, for example, at an angle, Θ, in the range of between 0 and 90 degrees. In FIG. 5E, a row of fins 56 is illustrated that each lie in a plane 59e that is oriented non-parallel to the tangent line or plane T-T. The fins 56 can alternatively be located at the lower surface 42 and also have an arcuate shape that conforms to the bone. The plate can be a periarticular plate or a straight plate. The plate may have a head portion that is contoured to conform to a particular bone surface, such as a metaphysis or diaphysis, that flares out from the shaft portion, that forms an L-shape, T-shape, Y-shape, with the shaft portion, or that forms any other appropriate shape to fit the bone to be treated.

The bone plate 40 can be made from metal, a resorbable or non-resorbable plastic, ceramic, or composite materials. Suitable materials may include, for example, titanium, stainless steel, cobalt chrome, polyetheretherketone (PEEK), polyethylene, ultra high molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a body.

Turning now to the methods of implantation, the surgeon accesses the surgical site of interest, which can be an internal site at which a bone fracture is located that requires stabilization to ensure proper healing. The fracture may be reduced with conventional forceps and guides (which are known to those in the art), and a bone plate 40 of appropriate size and shape is placed over the fracture site. In some instances, the bone plate 40 may be temporarily secured to the bone 4 using provisional fixation pins. The provisional fixation pins may be used through either the provisional pin openings 102, or any other opening in the plate 40. Provisional fixation provides for temporarily securing the bone plate 40 to the bone 4 before placing fixation screws through the bone plate 40, so that one can be certain the bone plate 40 is properly positioned before placing bone screws for permanent fixation of the bone plate 40 to the bone 4. Moreover, with provisional fixation, x-rays can be taken of the bone plate/construct without excess instruments in the field of view.

Once the plate 40 is secured at a desired location in relation to the fracture (typically using one or more provisional fixation pins, although any other appropriate method may be used), the surgeon then identifies an insertion angle at which the fastener 90 is to be inserted through a selected opening 50 and driven into bone material 4. If the bone plate 40 includes more than one opening 50, the surgeon also selects the specific opening 50 to be used. After selecting the desired insertion angle and the opening 50, the surgeon inserts the shaft 92 of the fastener 90 through the opening 50 until the tip contacts bone material 4. In some cases, a hole may need to be drilled or tapped into the bone 4 along the insertion angle to facilitate the initial tapping or insertion of the fastener 90. The surgeon then uses an appropriate driving tool in the bore 18 of the head 94 to manipulate the fastener 90 into place.

Because the fastener 90 can be inserted at angles up to about 60 degrees from perpendicular to the lower surface of the plate, the fastener 90 can be used to grab and/or secure bone fragments that are out of line with the traditional angle at which a locking screw would normally be inserted. The surgeon may need to toggle or maneuver the fastener 90 in order to secure and draw in displaced bone fragments.

Once the bone fragment is secured, the fastener 90 is ready to be secured to the plate 40. As the fastener 90 is driven further into bone 4, it is also drawn further into the plate 40. As the threads 98 of the fastener head 94 begin to contact the fins 56, the fins 56 engage within the threads 98 to hold the fastener 90 in place at the desired insertion angle. The action of engagement between the fins 56 and the threads 98 rigidly affixes the fastener 90 to the bone plate 40 at the desired insertion angle.

The surgeon may then use traditional locking and/or non-locking screws in other openings on the plate 40. This can help further secure the bone plate 40 to the bone fracture if needed.

Once all the fasteners and/or screws are placed, the surgeon may place covers over the unused openings, particularly if there are any unused openings that cross the fracture, to strengthen the plate 40. Additionally or alternatively, the surgeon may use bone graft material, bone cement, bone void filler, and any other material to help heal the bone.

In practice, a first screw is initially inserted through a bone plate 40 and into a bone 4 on one side of a fracture and then a second screw is inserted through the bone plate 40 on the opposite side of the fracture. In particular, after the first screw is in place, an axial compression screw is inserted through a hole in the bone plate 40 on a side of the fracture opposite the side of the first screw. The compression screw may be inserted through the hole and into the bone 4 such that as the compression screw is fully inserted, the bone plate 40 is drawn over to a desired position. By moving the bone plate 40, the tissue is pulled together to reduce the fracture. Once the compression screw has been used to move the bone plate 40 into the desired position, the compression screw may be removed from the bone 4 and bone plate 40 and a locking screw may be inserted through the opening 50 in the bone plate 40 and in the bone 4 in the space formerly occupied by the compression screw. The locking screw can then be tightened to lock the plate 40 into position. The replacement of the compression screw with the locking screw is not required, but a locking screw may provide more stability and rigid fixation than leaving the compression screw in place. In some modes of operation, a locking screw is placed directly in a locking hole without first inserting a compression screw in the hole.

A number of implementations of the invention have been described. Nevertheless, it will be understood that various modifications may be made without departing from the spirit and scope of the invention. Accordingly, other implementations are within the scope of the following claims. For example, locking screws, non-locking screws, or other fasteners may be used. One or more openings having a non-perpendicular orientation of the central axis 52 and/or the non-parallel orientation of the plane 59 can be employed to receive a fastener in implants other than plates, such as in an acetabular cup or glenoid base component, to increase the useful range of possible insertion angles of the fastener. According to another implementation, the head of the screw 94 can include the fins 56 and the opening 50 can be threaded, with the opening having a non-perpendicular orientation of its central axis 52 and/or the plane 59 defined by the fins 56 having a non-parallel orientation.

What is claimed is:

1. An implant comprising:
   a first surface;
   a second surface; and
   at least one opening extending from the first surface to the second surface, the at least one opening including:
      a central axis;
      an inner surface including a plurality of fins defining a circumferential edge to contact a head of a bone fastener in use; and
      a plurality of threads formed on the inner surface;
   wherein the at least one opening is configured to secure the bone fastener with respect to the implant.

2. The implant of claim 1, wherein the central axis is non-perpendicular to a tangent of a projection of the first surface across the opening, the tangent defined at an intersection between the central axis and the projected first surface.

3. The implant of claim 2, wherein the plurality of fins are oriented along a plane, wherein each of the fins has a base and a tip, wherein each of the fins extends through the plane from the base to the tip, and wherein the tip of each fin has a rounded, convex curve that lies in the plane.

4. The implant of claim 3, wherein the plane along which the plurality of fins is oriented is nonparallel to the tangent.

5. The implant of claim 4, wherein the plane is perpendicular to the central axis.

6. The implant of claim 1, wherein the plurality of fins are adapted and configured to deform in order to secure a position of the head of the bone fastener inserted into the at least one opening.

7. The implant of claim 1, wherein the implant is a bone plate, the first surface is a bone contacting surface, and the plurality of threads are positioned closer to the bone contacting surface than the plurality of fins.

8. The implant of claim 7, wherein the bone contacting surface is adapted to contact a distal femur, a proximal femur, a distal tibia, a proximal tibia, a proximal humerus, a distal humerus, a clavicle, a fibula, an ulna, a radius, a distal radius, a rib, pelvis, a vertebra, bones of a foot, or bones of a hand.

9. The implant of claim 7, wherein the central axis is non-perpendicular to the bone contacting surface, the plurality of fins are oriented along a plane, wherein the plane is oriented nonparallel to the bone contacting surface.

10. The implant of claim 9, wherein the central axis is orientated an angle relative to the bone contacting surface, the angle being fifteen degrees.

11. The implant of claim 1, wherein each of the plurality of fins includes a tip having a rounded, convex curve, each of the plurality of fins extends toward the central axis of the opening from a base to the rounded, convex curve, and each of the plurality of fins has a width in the plane that decreases from the base to the tip in a direction toward the central axis of the opening.

12. The implant of claim 1, wherein the implant has at least 3, but no more than 10, fins integrally connected to, and protruding from, the inner surface.

13. The implant of claim 1, wherein the plurality of fins are provided as a series of inwardly protruding fins that are adapted to secure the head of the bone fastener in place at varying angles, wherein the head is threaded, wherein adjacent fins in the series of inwardly protruding fins cooperate to form a curved, concave indentation along the plane.

14. The implant of claim 1, wherein the opening is adapted to receive the bone fastener without being tapped by the bone fastener, wherein the plurality of fins are deflectable relative to the head of the bone fastener when the bone fastener is inserted into the opening such that the bone fastener can be inserted and retained at any one of a plurality of angles relative to the opening.

15. The implant of claim 14, wherein the plurality of fins are deflectable so that the plurality fins are interposed between threads of the bone fastener.

16. A variable angle locking implant comprising:
    a bone plate having:
       an end portion;
       a shaft portion that extends along a longitudinal axis;
       a lower bone contacting surface;
       an upper surface; and
       an opening including:
          a central axis, the opening extending along the central axis from the lower bone contacting surface to the upper surface;
          an inner surface including a plurality of fins oriented along a plane, wherein each of the fins has a base and a tip, wherein each of the fins extends through the plane from the base to the tip, the tips of the plurality of fins collectively defining a circumferential edge to contact a head of a bone fastener in use; and
          a plurality of threads formed on the inner surface.

17. The variable angle locking implant of claim 16, wherein the central axis is non-perpendicular to the lower bone contacting surface and the plane is oriented nonparallel to the lower bone contacting surface.

18. The variable angle locking implant of claim 16, wherein the plurality of threads are positioned closer to the lower bone contacting surface than the plurality of fins.

* * * * *